(12) United States Patent
Yu et al.

(10) Patent No.: US 9,885,561 B2
(45) Date of Patent: Feb. 6, 2018

(54) OPTICAL INSPECTION SYSTEM

(71) Applicant: Test Research, Inc., Taipei (TW)

(72) Inventors: Liang-Pin Yu, New Taipei (TW);
Kuang-Pu Wen, Hsinchu (TW);
Yeong-Feng Wang, Taipei (TW)

(73) Assignee: Test Research, Inc., Taipei (TW)

( * ) Notice: Subject to any disclaimer, the term of this patent is extended or adjusted under 35 U.S.C. 154(b) by 252 days.

(21) Appl. No.: 14/570,296

(22) Filed: Dec. 15, 2014

(65) Prior Publication Data

US 2016/0169812 A1    Jun. 16, 2016

(51) Int. Cl.
*H04N 9/47* (2006.01)
*G01B 11/24* (2006.01)
*G01N 21/88* (2006.01)

(52) U.S. Cl.
CPC ......... *G01B 11/24* (2013.01); *G01N 21/8806* (2013.01); *G01N 2201/06113* (2013.01)

(58) Field of Classification Search
CPC ...................................... G01B 11/24
See application file for complete search history.

(56) References Cited

U.S. PATENT DOCUMENTS

| | | |
|---|---|---|
| 5,042,944 A | 8/1991 | Lukasiewicz et al. |
| 2007/0195314 A1* | 8/2007 | Morimoto .............. G01B 11/24 356/236 |
| 2008/0165820 A1* | 7/2008 | Fukuda .............. B29D 11/0074 372/53 |
| 2012/0310083 A1* | 12/2012 | Friedman ................. A61B 3/10 600/431 |
| 2013/0041216 A1* | 2/2013 | McDowall ............... G02B 5/04 600/109 |
| 2014/0168417 A1 | 6/2014 | Hsieh et al. |
| 2014/0376003 A1* | 12/2014 | Keranen .............. G01B 11/245 356/610 |

FOREIGN PATENT DOCUMENTS

| | | |
|---|---|---|
| DE | 102004034160 A1 | 2/2006 |
| DE | 102005031957 A1 | 1/2007 |
| JP | 08-240408 A | 9/1996 |
| JP | 11-211443 A | 8/1999 |
| JP | 2000-234907 A | 8/2000 |
| JP | 2000-294610 A | 10/2000 |
| JP | 2005-043371 | 2/2005 |

(Continued)

*Primary Examiner* — Tracy Y Li
(74) *Attorney, Agent, or Firm* — Merchant & Gould P.C.

(57) ABSTRACT

An optical inspection system includes a first optical module and a second optical module. The first optical module includes a first light source having a first optical axis and a first image capturing unit having a first image capturing axis. The first optical axis and the first image capturing axis are symmetric relative a normal line of an inspection plane. A first angle is formed between the first optical axis and the first image capturing axis. The second optical module includes a second light source having a second optical axis and a second image capturing unit having a second image capturing axis. The second optical axis and the second image capturing axis are symmetric relative to the normal line. A second angle is formed between the second optical axis and the second image capturing axis and is different from the first angle.

20 Claims, 7 Drawing Sheets

(56) References Cited

FOREIGN PATENT DOCUMENTS

| | | |
|---|---|---|
| JP | 2007-033099 A | 2/2007 |
| JP | 2009-516840 A | 4/2009 |
| JP | 2011-515703 A | 5/2011 |
| JP | 4789438 B2 | 10/2011 |
| KR | 100722245 B1 | 5/2007 |
| TW | 201344151 A | 11/2013 |
| WO | 2013/058710 A1 | 4/2013 |
| WO | 2014/087046 A1 | 6/2014 |

* cited by examiner

OPTICAL INSPECTION SYSTEM

BACKGROUND

Technical Field

The present disclosure relates to an optical inspection system, and more particularly, to a three-dimensional measurement system.

Description of Related Art

In general, methods for measuring the three-dimensional shape of a DUT (device under test) can be divided into contact type methods and non-contact type methods. Non-contact type methods typically involve projecting a laser spot, a laser beam, or a structured (e.g., striped) light onto a DUT and then respectively scanning point-by-point, line-by-line, or the deformed stripes. Based on the triangular relationship among the light source, the DUT, and the imaging position, the height values of the three-dimensional shape of the DUT can be calculated.

Figure 7:
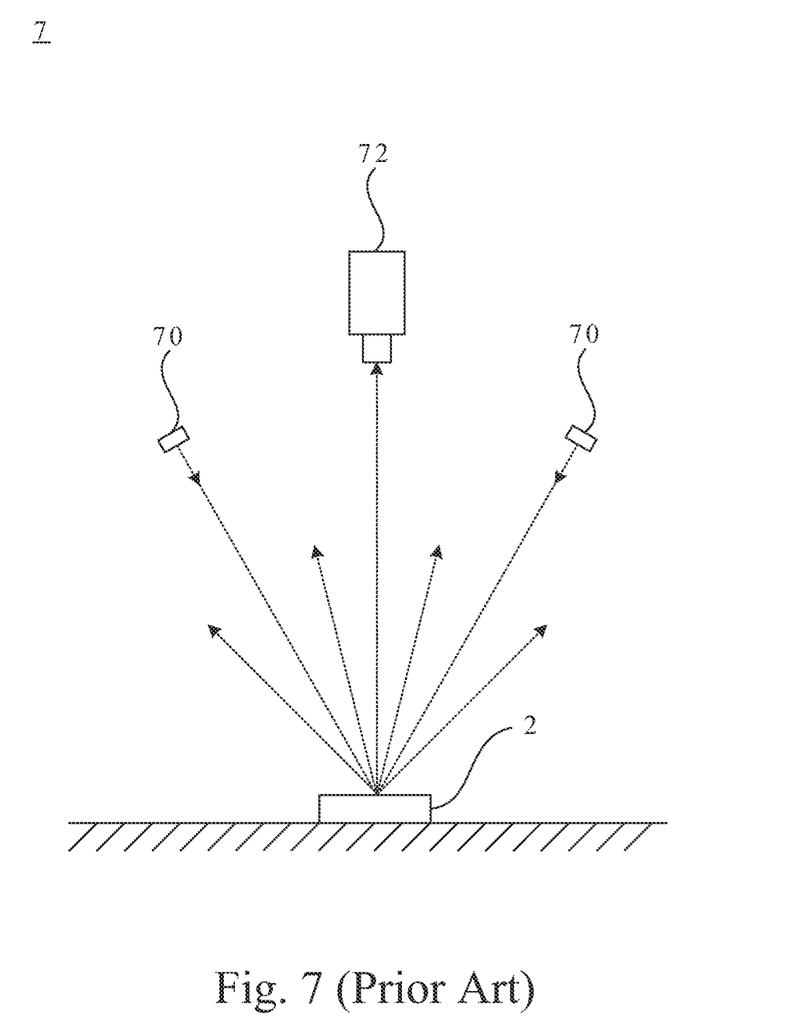
FIG. 7 is a schematic diagram illustrating a conventional optical inspection system.

FIG. 7 is a schematic diagram illustrating a conventional optical inspection system 7. As shown in FIG. 7, the optical inspection system 7 has two light sources 70 and a camera 72. The light sources 70 are respectively located at two sides of a DUT 2 and emit light toward the DUT 2. The camera 72 is located right over the DUT 2 for receiving light reflected from the DUT 2 to thereby generate corresponding images of the DUT 2.

However, the conventional optical inspection system 7 cannot be applied to certain DUTs, such as objects having mirror surfaces. With such objects with mirror surfaces, a large amount of the emitted light cannot be reflected to the camera 72, since this light is reflected from the objects in a manner that follows the law of reflection. Therefore, the intensity of the reflected light received by the camera 72 is too low, so that image contrast is poor, thus affecting subsequent algorithmic interpretations. Even if the optical inspection system 7 can be modified to be in accordance with the law of reflection and thereby obtain better image contrast, problems of shadows and image distortion of the captured images will occur. The problem of image distortion can be compensated for using an algorithm, but the problem of shadows cannot be overcome.

Accordingly, those in the industry are endeavoring to provide an optical inspection system that is able to solve the aforementioned problems.

SUMMARY

The disclosure provides an optical inspection system for inspecting a DUT (device under test). The optical inspection system includes a first optical module and a second optical module. The first optical module includes a first light source and a first image capturing unit. The first light source has a first optical axis. The first image capturing unit has a first image capturing axis. The first optical axis and the first image capturing axis are symmetric relative a normal line of an inspection plane on the DUT. A first angle is formed between the first optical axis and the first image capturing axis. The second optical module includes a second light source and a second image capturing unit. The second light source has a second optical axis. The second image capturing unit has a second image capturing axis. The second optical axis and the second image capturing axis are symmetric relative to the normal line. A second angle is formed between the second optical axis and the second image capturing axis, and the second angle is different from the first angle.

In an embodiment of the disclosure, the first light source and the second image capturing unit are located at a side of the normal line, and the second light source and the first image capturing unit are located at another side of the normal line.

In an embodiment of the disclosure, the first and second angles are ranged from 55 to 65 degrees.

In an embodiment of the disclosure, the first and second light sources emit unpolarized light or polarized light.

In an embodiment of the disclosure, light emitted by the first light source generates a first fringe pattern on the DUT. The first fringe pattern has a first stripe pitch. Light emitted by the second light source generates a second fringe pattern on the DUT. The second fringe pattern has a second stripe pitch equal to the first stripe pitch.

In an embodiment of the disclosure, light emitted by the first light source generates a first fringe pattern on the DUT. The first fringe pattern has a first stripe pitch. Light emitted by the second light source generates a second fringe pattern on the DUT, and the second fringe pattern has a second stripe pitch different from the first stripe pitch.

The disclosure further provides an optical inspection system for inspecting a DUT. The optical inspection system includes a first optical module and a second optical module. The first optical module includes a first light source, a first image capturing unit, and a first filter. The first light source has a first optical axis. The first image capturing unit has a first image capturing axis. The first optical axis and the first image capturing axis are symmetric relative a normal line of an inspection plane on the DUT. A first angle is formed between the first optical axis and the first image capturing axis. The first filter is located on the first image capturing axis and has a first transmission spectrum. The second optical module includes a second light source, a second image capturing unit, and a second filter. The second light source has a second optical axis. The second image capturing unit has a second image capturing axis. The second optical axis and the second image capturing axis are symmetric relative to the normal line. A second angle is formed between the second optical axis and the second image capturing axis, and the second angle is different from the first angle. The second filter is located on the second image capturing axis and has a second transmission spectrum shifted away from the first transmission spectrum. The first filter is configured to transmit most of light emitted by the first light source and to reflect most of light emitted by the second light source. The second filter is configured to reflect most of the light emitted by the first light source and to transmit most of light emitted by the second light source.

In an embodiment of the disclosure, the light emitted by the first light source has a first triplet substantially matching the first transmission spectrum. The light emitted by the second light source has a second triplet substantially matching the second transmission spectrum.

In an embodiment of the disclosure, the first light source, the second filter, and the second image capturing unit are located at a side of the normal line. The second light source, the first filter, and the first image capturing unit are located at another side of the normal line.

The disclosure further provides an optical inspection system for inspecting a DUT. The optical inspection system includes a first optical module and a second optical module. The first optical module includes a first image capturing unit, a first filter, and a first light source. The first image capturing unit has a first image capturing axis. The first filter is located on the first image capturing axis and has a first transmission spectrum. The first light source is used to emit light toward the first filter. The first filter is configured to reflect most of light emitted by the first light source. The reflected light of the first light source has a first optical axis substantially coinciding with the first image capturing axis. The second optical module includes a second image capturing unit, a second filter, and a second light source. The second image capturing unit has a second image capturing axis. The second image capturing axis and the first image capturing axis are symmetric relative to a normal line of an inspection plane on the DUT. The second filter is located on the second image capturing axis and has a second transmission spectrum shifted away from the first transmission spectrum. The second light source is used to emit light toward the second filter. The second filter is configured to reflect most of light emitted by the second light source. The reflected light of the second light source has a second optical axis substantially coinciding with the second image capturing axis. The first filter is further configured to transmit most of the light emitted by the second light source. The second filter is further configured to transmit most of the light emitted by the first light source.

In an embodiment of the disclosure, the light emitted by the first light source has a first triplet substantially matching the second transmission spectrum. The light emitted by the second light source has a second triplet substantially matching the first transmission spectrum.

In an embodiment of the disclosure, the first optical module is located at a side of the normal line, and the second optical module is located at another side of the normal line.

In an embodiment of the disclosure, a first angle is formed between the first image capturing axis and the second image capturing axis. The optical inspection system further includes a third optical module and a fourth optical module. The third optical module includes a third image capturing unit, a third filter, and a third light source. The third image capturing unit has a third image capturing axis. The third filter is located on the third image capturing axis and has the first transmission spectrum. The third light source is used to emit light toward third filter. The third filter is configured to reflect most of light emitted by the third light source. The reflected light of the third light source has a third optical axis substantially coinciding with the third image capturing axis. The fourth optical module includes a fourth image capturing unit, a fourth filter, and a fourth light source. The fourth image capturing unit has a fourth image capturing axis. The fourth image capturing axis and the third image capturing axis are symmetric relative to the normal line. A second angle is formed between the third image capturing axis and the fourth image capturing axis, and the second angle is different from the first angle. The fourth filter is located on the fourth image capturing axis and has the second transmission spectrum. The fourth light source is used to emit light toward the fourth filter. The fourth filter is configured to reflect most of light emitted by the fourth light source. The reflected light of the fourth light source has a fourth optical axis substantially coinciding with the fourth image capturing axis. The third filter is further configured to transmit most of the light emitted by the fourth light source. The fourth filter is further configured to transmit most of the light emitted by the third light source.

In an embodiment of the disclosure, the light emitted by the third light source has a first triplet substantially matching the second transmission spectrum. The light emitted by the fourth light source has a second triplet substantially matching the first transmission spectrum.

In an embodiment of the disclosure, the third optical module is located at a side of the normal line, and the fourth optical module is located at another side of the normal line.

In an embodiment of the disclosure, the third and fourth light sources emit unpolarized light or polarized light.

Accordingly, the optical inspection system of the disclosure arranges the optical axis of each of the light sources and the image capturing axis of the corresponding image capturing unit to be symmetric relative to the normal line of the inspection plane, so that even if the DUT has a mirror surface at the inspection plane, a large amount of the emitted light of each light source can be reflected to the corresponding image capturing unit. The optical inspection system of the disclosure further locates the light sources at two opposite sides of the DUT relative to the normal line respectively, so that even if the images captured by the image capturing units have shadows at different locations, the images can be further analyzed and synthesized to obtain a synthetic image without shadows, and thus the problem of shadows can be solved. Furthermore, the optical inspection system of the disclosure is configured such that the angle between the optical axis and the corresponding image capturing axis in an optical module is different from that in another optical module, so as to improve the inspecting capability of particles and short circuit problems. Moreover, by adjusting the above-mentioned angles, the measurement range of the optical inspection system can be enlarged. In addition, by using filters that each only allows for transmitting most of the light emitted by the corresponding light source, all of the image capturing units can capture images at the same time, so as to improve the inspection efficiency of the optical inspection system.

It is to be understood that both the foregoing general description and the following detailed description are by examples, and are intended to provide further explanation of the disclosure as claimed.

BRIEF DESCRIPTION OF THE DRAWINGS

The disclosure can be more fully understood by reading the following detailed description of the embodiments, with reference made to the accompanying drawings as follows.

DETAILED DESCRIPTION

Reference will now be made in detail to the present embodiments of the disclosure, examples of which are illustrated in the accompanying drawings. Wherever possible, the same reference numbers are used in the drawings and the description to refer to the same or like parts.

Figure 1:
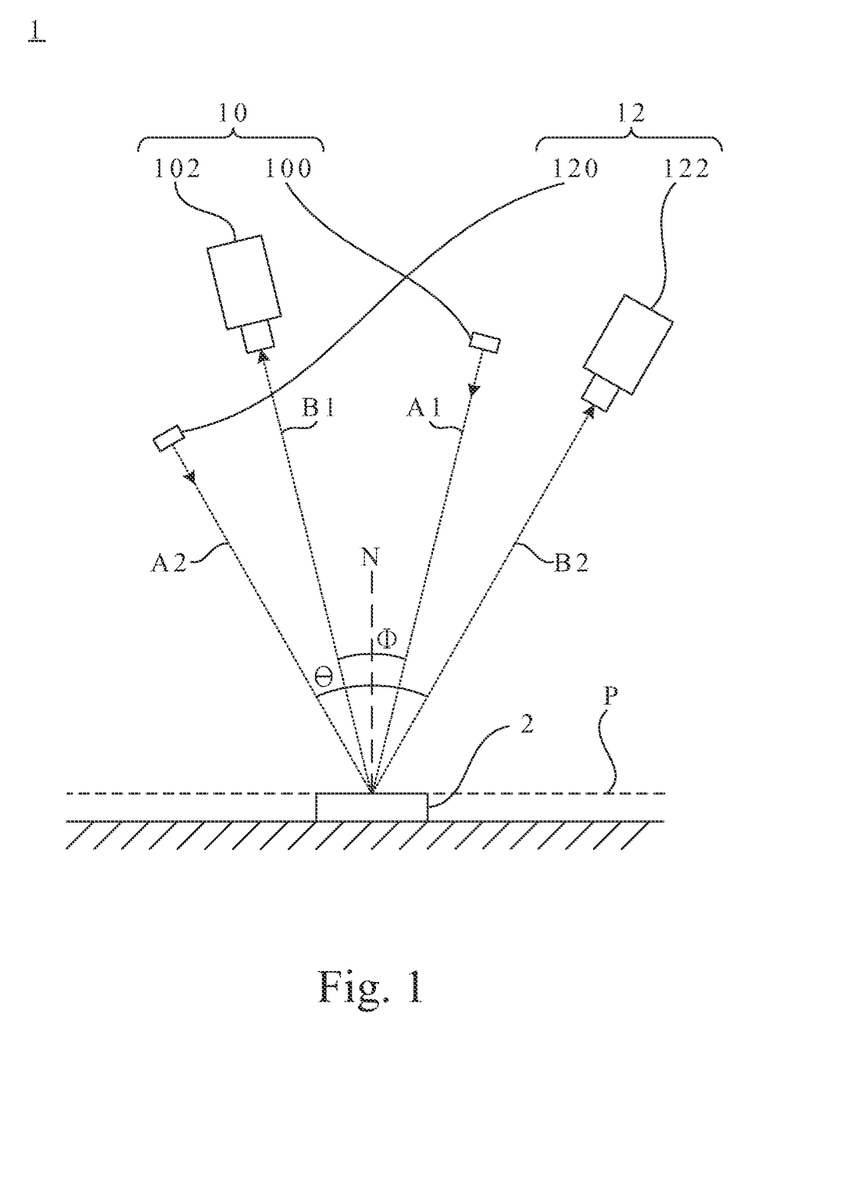
FIG. 1 is a schematic diagram illustrating an optical inspection system according to an embodiment of the disclosure.

FIG. 1 is a schematic diagram illustrating an optical inspection system 1 according to an embodiment of the disclosure. Referring to FIG. 1, the optical inspection system 1 is used to inspect a DUT (device under test) 2. The optical inspection system 1 includes a first optical module 10 and a second optical module 12. The first optical module 10 includes a first light source 100 and a first image capturing unit 102. The first light source 100 has a first optical axis A1 aligned with the DUT 2. That is, the light exit surface of the first light source 100 substantially faces toward the DUT 2. The first image capturing unit 102 has a first image capturing axis B1 aligned with the DUT 2. That is, the light receiving surface of the first image capturing unit 102 substantially faces toward the DUT 2. The first optical axis A1 and the first image capturing axis B1 are symmetric relative a normal line N of an inspection plane P on the DUT 2. A first angle $\varphi$ is formed between the first optical axis A1 and the first image capturing axis B1.

The second optical module 12 includes a second light source 120 and a second image capturing unit 122. The second light source 120 has a second optical axis A2 aligned with the DUT 2. That is, the light exit surface of the second light source 120 substantially faces toward the DUT 2. The second image capturing unit 122 has a second image capturing axis B2 aligned with the DUT 2. That is, the light receiving surface of the second image capturing unit 122 substantially faces toward the DUT 2. The second optical axis A2 and the second image capturing axis B2 are symmetric relative to the normal line N. A second angle $\theta$ is formed between the second optical axis A2 and the second image capturing axis B2, and the second angle $\theta$ is different from the first angle $\varphi$.

In the embodiment of the disclosure, even if the DUT 2 has a mirror surface at the inspection plane P, a large amount of the emitted light of the first light source 100 can be reflected to the first image capturing unit 102 because the arrangement of the first optical axis A1 and the first image capturing axis B1 is in accordance with the law of reflection, and similarly, a large amount of the emitted light of the second light source 120 can be reflected to the second image capturing unit 122 because the arrangement of the second optical axis A2 and the second image capturing axis B2 is also in accordance with the law of reflection.

Furthermore, the optical inspection system 1 of this embodiment is configured such that the first angle $\varphi$ between the first optical axis A1 and the first image capturing axis B1 of the first optical module 10 is different from the second angle $\theta$ between the second optical axis A2 and the second image capturing axis B2 of the second optical module 12, so as to improve the inspecting capability of particles and short circuit problems on the DUT 2.

In an embodiment of the disclosure, the first and second angles $\varphi$, $\theta$ are ranged from 55 to 65 degrees, but the disclosure is not limited in this regard.

In the embodiment of the disclosure, the first light source 100 and the second image capturing unit 122 are located at a side of the normal line N (i.e., the right side of the normal line N), and the second light source 120 and the first image capturing unit 102 are located at another side of the normal line N (i.e., the left side of the normal line N). That is, the first light source 100 and the second light source 120 are respectively located at two opposite sides of the DUT 2 relative to the normal line N. In some embodiments, the first image capturing unit 102 and the second image capturing unit 122 capture images sequentially. For example, the first light source 100 emits light toward the DUT 2 and the first image capturing unit 102 captures an image of the DUT 2 at the same time, and then the second light source 120 emits light toward the DUT 2 and the second image capturing unit 122 capture another image of the DUT 2 at the same time. Through such operation, even if the left part of the image captured by the first image capturing unit 102 and the right part of the image captured by the second image capturing unit 122 have shadows, the captured images can be analyzed and synthesized to obtain a synthetic image without shadows. The three-dimensional shape of the DUT 2 can then be calculated from the synthetic image by using an algorithm. Accordingly, the problem of shadows can be solved by the optical inspection system 1 of this embodiment.

In an embodiment of the disclosure, each of the first and second light sources 100, 120 emits unpolarized light. Although the first light source 100 and the second light source 120 emit unpolarized light toward the DUT 2 with different incident angles, a better uniformity can be obtained.

In an embodiment of the disclosure, each of the first and second light sources 100, 120 emits polarized light. In order to obtain better image contrast when analyzing certain defects or sloped surfaces, polarized light can be used.

In an embodiment of the disclosure, the light emitted by the first light source 100 generates a first fringe pattern consisting of many stripes on the DUT 2, and the light emitted by the second light source 120 generates a second fringe pattern consisting of many stripes on the DUT 2. Both the first fringe pattern and the second fringe pattern are equal-spaced-multi-line patterns. Seen from different viewpoints (i.e., from the first image capturing unit 102 and the second image capturing unit 122), the first fringe pattern and the second fringe pattern appear geometrically distorted due to the surface shape of the DUT 2. There are several depth cues contained in the observed stripe patterns. The displacement of the stripes allows for an exact retrieval of the three-dimensional coordinates of any details on the surface of the DUT 2. For this purpose, the individual stripe has to be identified, which can for example be accomplished by tracing or counting stripes (pattern recognition method).

Figure 2:
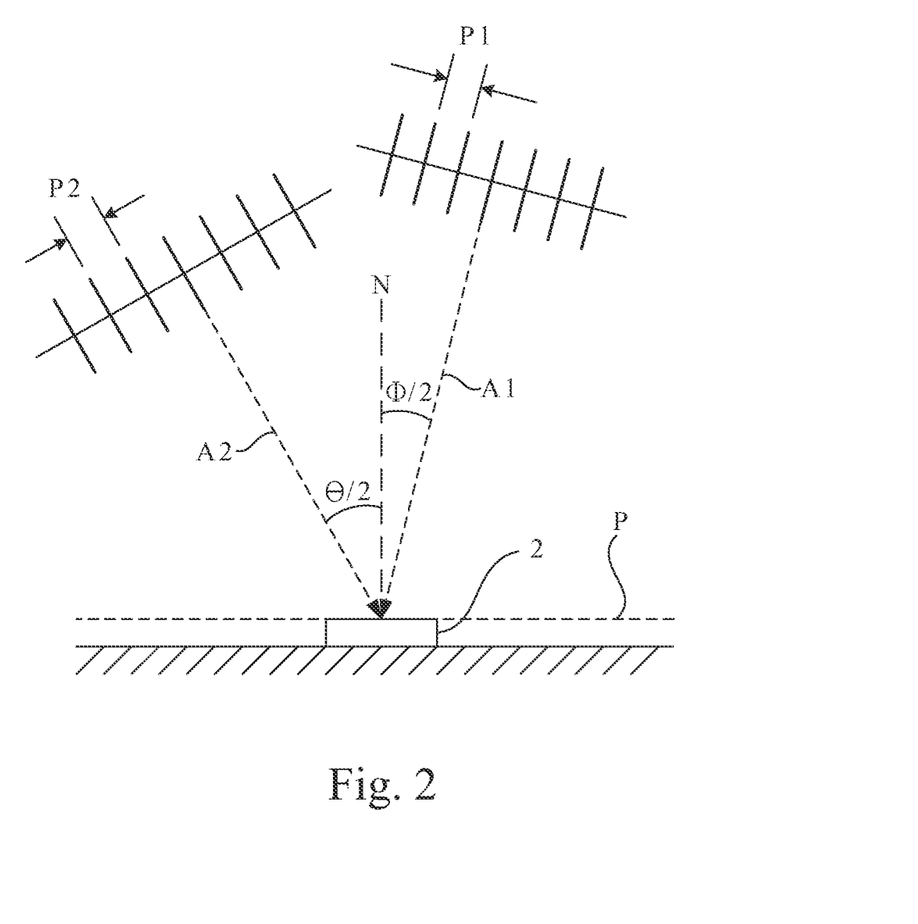
FIG. 2 is a schematic diagram illustrating the measurement principle of a first fringe pattern and a second fringe pattern.

FIG. 2 is a schematic diagram illustrating the measurement principle of the first fringe pattern and the second fringe pattern. As shown in FIG. 2, both of the projection of the first fringe pattern with a first stripe pitch P1 and the projection of the second fringe pattern with a second stripe pitch P2 can be used as the smallest unit of measure individually, and using the smallest unit of measure and a phase-shift method can effectively solve space height (i.e., the three-dimensional shape of the DUT 2). At present, the three-dimensional shape of the DUT 2 can be reconstructed from the reflection images thereof based on the phase-shift method. In the phase-shift method, a number of at least 3, typically about 10, reflection images are taken with slightly shifted stripes. The first theoretical deductions of this method relied on stripes with a sine wave shaped intensity modulation, but the methods work with "rectangular" modulated stripes, as delivered from LCD or DLP displays as well. By phase shifting, the surface detail of, for example, 1/10 the stripe pitch can be resolved. These reflection images can be analyzed taking into consideration forms of the structured light emitted by the first light source 100 and the second light source 120 and the height of the inspection plane P to reconstruct the three-dimensional shape of the DUT 2.

In the embodiment of the disclosure, the second stripe pitch P2 is different from the first stripe pitch P1. In another embodiment of the disclosure, the second stripe pitch P2 is equal to the first stripe pitch P1. By collocating the emitted light with different incident angles (i.e., the angles φ/2, θ/2 in FIG. 2), the measurement range of the optical inspection system 1 can be enlarged.

Figure 3:
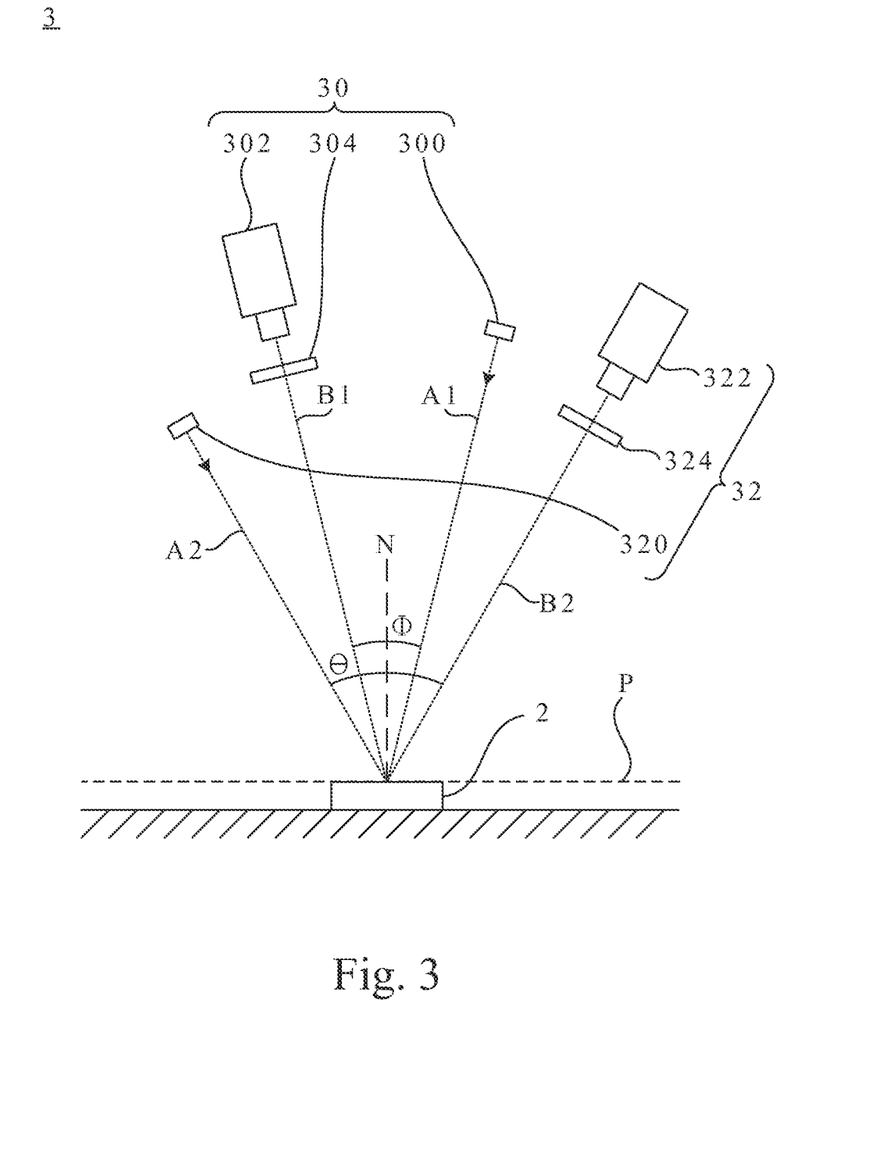
FIG. 3 is a schematic diagram illustrating an optical inspection system according to another embodiment of the disclosure.

FIG. 3 is a schematic diagram illustrating an optical inspection system 3 according to another embodiment of the disclosure. As shown in FIG. 3, the optical inspection system 3 is also used to inspect a DUT 2. The optical inspection system 3 includes a first optical module 30 and a second optical module 32. The first optical module 30 includes a first light source 300, a first image capturing unit 302, and a first filter 304. The first light source 300 has a first optical axis A1 aligned with the DUT 2. The first image capturing unit 302 has a first image capturing axis B1 aligned with the DUT 2. The first optical axis A1 and the first image capturing axis B1 are symmetric relative a normal line N of an inspection plane P on the DUT 2. A first angle φ is formed between the first optical axis A1 and the first image capturing axis B1. The first filter 304 is located on the first image capturing axis B1 and has a first transmission spectrum.

The second optical module 32 includes a second light source 320, a second image capturing unit 322, and a second filter 324. The second light source 320 has a second optical axis A2 aligned with the DUT 2. The second image capturing unit 322 has a second image capturing axis B2 aligned with the DUT 2. The second optical axis A2 and the second image capturing axis B2 are symmetric relative to the normal line N of the inspection plane P on the DUT 2. A second angle θ is formed between the second optical axis A2 and the second image capturing axis B2. The second filter 324 is located on the second image capturing axis B2 and has a second transmission spectrum shifted away from the first transmission spectrum.

The first filter 304 is configured to transmit most of the light emitted by the first light source 300 and to reflect most of the light emitted by the second light source 320, and the second filter 324 is configured to reflect most of the light emitted by the first light source 300 and to transmit most of the light emitted by the second light source 320. In other words, the transmittance of the light emitted by the first light source 300 through the first filter 304 is much greater than the transmittance of the light emitted by the second light source 320 through the first filter 304, and the transmittance of the light emitted by the first light source 300 through the second filter 324 is much smaller than the transmittance of the light emitted by the second light source 320 through the second filter 324.

Figure 4A:
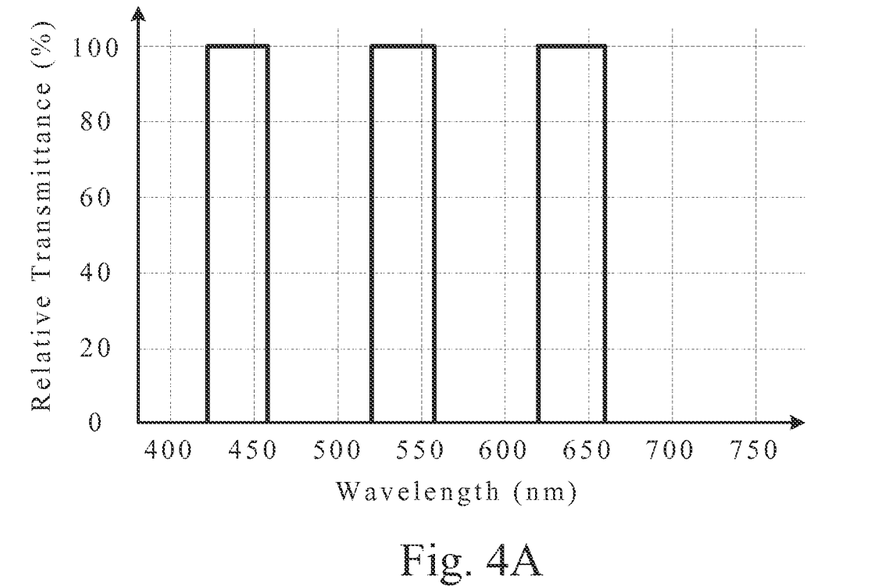
FIG. 4A is a diagram of relative transmittance vs. wavelength with respect to a first filter in FIG. 3.
Figure 4B:
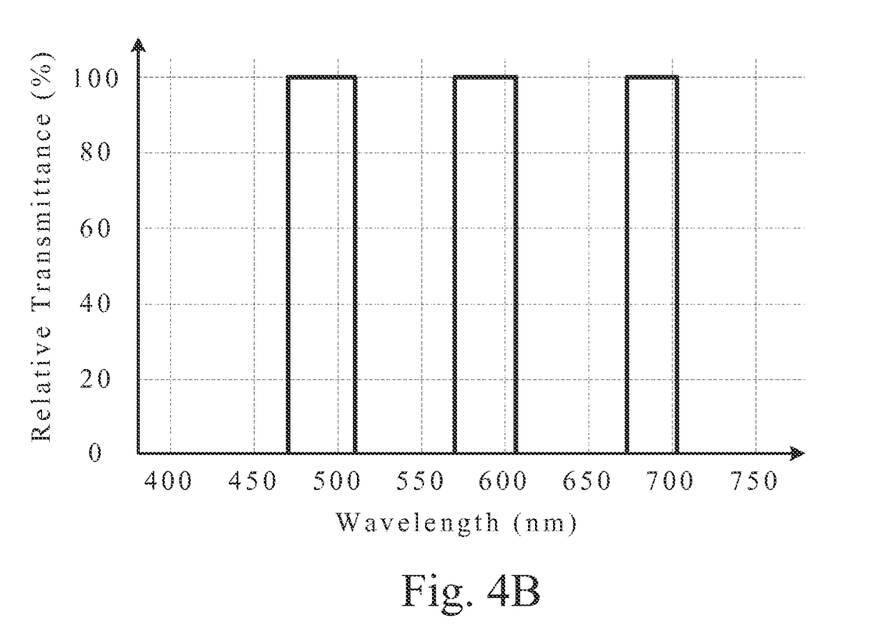
FIG. 4B is a diagram of relative transmittance vs. wavelength with respect to a second filter in FIG. 3.

FIG. 4A is a diagram of relative transmittance vs. wavelength with respect to the first filter 304 in FIG. 3. FIG. 4B is a diagram of relative transmittance vs. wavelength with respect to the second filter 324 in FIG. 3. As shown in FIG. 4A and FIG. 4B, it is clear that the second transmission spectrum is shifted away from the first transmission spectrum. For example, both of the first filter 304 and the second filter 324 have 39 layers of films (not shown). Each film has a specific transmission spectrum owing to the specific material and thickness thereof. Therefore, the first transmission spectrum can be controlled by adjusting materials or thicknesses of the films of the first filter 304, and the second transmission spectrum can be controlled by adjusting materials or thicknesses of the films of the second filter 324.

Figure 5A:
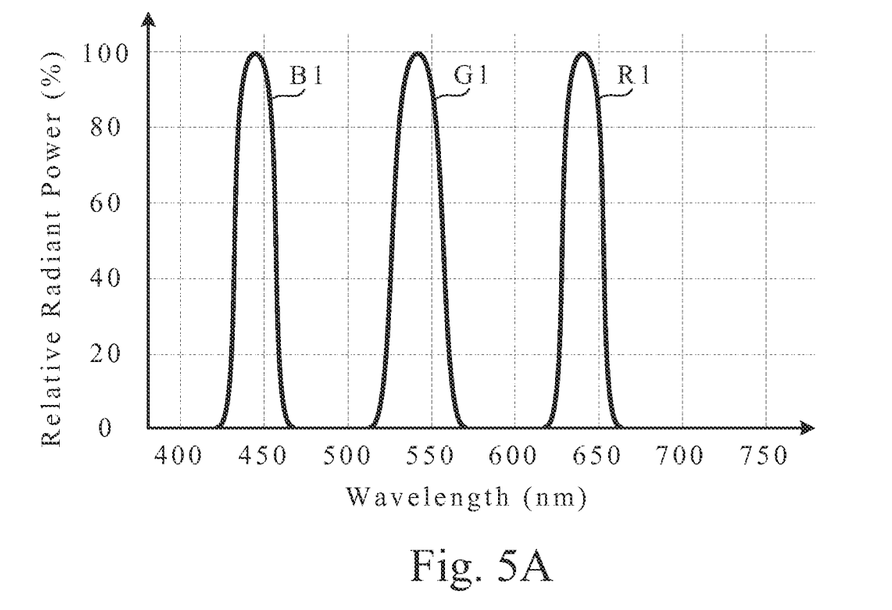
FIG. 5A is a diagram of relative radiant power vs. wavelength with respect to a first light source in FIG. 3.
Figure 5B:
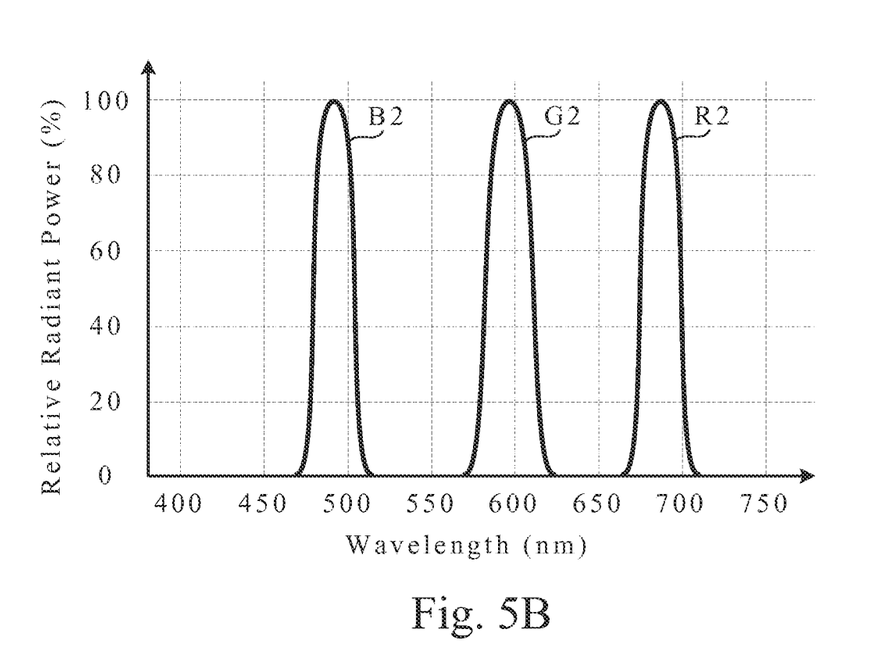
FIG. 5B is a diagram of relative radiant power vs. wavelength with respect to a second light source in FIG. 3.

FIG. 5A is a diagram of relative radiant power vs. wavelength with respect to the first light source 300 in FIG. 3. FIG. 5B is a diagram of relative radiant power vs. wavelength with respect to the second light source 320 in FIG. 3. As shown in FIG. 5A and FIG. 5B, the light emitted by the first light source 300 has a first triplet R1, G1, B1 substantially matching the first transmission spectrum of the first filter 304, and the light emitted by the second light source 320 has a second triplet R2, G2, B2 substantially matching the second transmission spectrum of the second filter 324. Accordingly, the purpose of configuring the first and second filters 304, 324 such that the first filter 304 transmits most of the light emitted by the first light source 300 and reflects most of the light emitted by the second light source 320, and the second filter 324 reflects most of the light emitted by the first light source 300 and transmits most of the light emitted by the second light source 320 can be achieved.

With the foregoing configuration, the first light source 300 and the second light source 320 can emit light toward the DUT 2 at the same time, and the first image capturing unit 302 and the second image capturing unit 322 can capture images of the DUT 2 at the same time, so as to improve the inspection efficiency of the optical inspection system 3.

In the embodiment of the disclosure, even if the DUT 2 has a mirror surface on the inspection plane P, a large amount of the emitted light of the first light source 300 can be reflected to the first image capturing unit 302 because the arrangement of the first optical axis A1 and the first image capturing axis B1 is in accordance with the law of reflection, and similarly, a large amount of the emitted light of the second light source 320 can be reflected to the second image capturing unit 322 because the arrangement of the second optical axis A2 and the second image capturing axis B2 is also in accordance with the law of reflection.

Furthermore, the optical inspection system 3 of this embodiment is configured such that the first angle φ between the first optical axis A1 and the first image capturing axis B1 of the first optical module 30 is different from the second angle θ between the second optical axis A2 and the second image capturing axis B2 of the second optical module 32, so as to improve the inspecting capability of particles and short circuit problems on the DUT 2.

In an embodiment of the disclosure, the first and second angles φ, θ are ranged from 55 to 65 degrees, but the disclosure is not limited in this regard.

In the embodiment of the disclosure, the first light source 300, the second filter 324, and the second image capturing unit 322 are located at a side of the normal line N (i.e., the right side of the normal line N), and the second light source 320, the first filter 304, and the first image capturing unit 302 are located at another side of the normal line N (i.e., the left side of the normal line N). That is, the first light source 300 and the second light source 320 are respectively located at two opposite sides of the DUT 2 relative to the normal line N. As mentioned above, the first image capturing unit 302 and the second image capturing unit 322 can capture images at the same time. Through such a configuration, even if the left part of the image captured by the first image capturing unit 302 and the right part of the image captured by the second image capturing unit 322 have shadows (because the first filter 304 and the second filter 324 only allow for transmitting of the light emitted by the first light source 300 and the second light source 320 respectively), the captured images can be analyzed and synthesized to obtain a synthetic image without shadows. The three-dimensional shape of the DUT 2 can then be calculated from the synthetic image by using an algorithm. Accordingly, the problem of shadows can also be solved by the optical inspection system 3 of this embodiment.

In an embodiment of the disclosure, each of the first and second light sources 300, 320 emits unpolarized light. Although the first light source 300 and the second light source 320 emit the unpolarized light toward the DUT 2 with different incident angles, a better uniformity can be obtained.

In an embodiment of the disclosure, each of the first and second light sources 300, 320 emits polarized light. In order to obtain better image contrast when analyzing certain defects or sloped surfaces, polarized light can be used.

In an embodiment of the disclosure, the light emitted by the first light source 300 generates a first fringe pattern consisting of many stripes on the DUT 2, and the light emitted by the second light source 320 generates a second fringe pattern consisting of many stripes on the DUT 2. The three-dimensional shape of the DUT 2 can be reconstructed from the reflection images thereof based on the pattern recognition method and the phase-shift method introduced above, and so these methods are not discussed here again.

Figure 6:
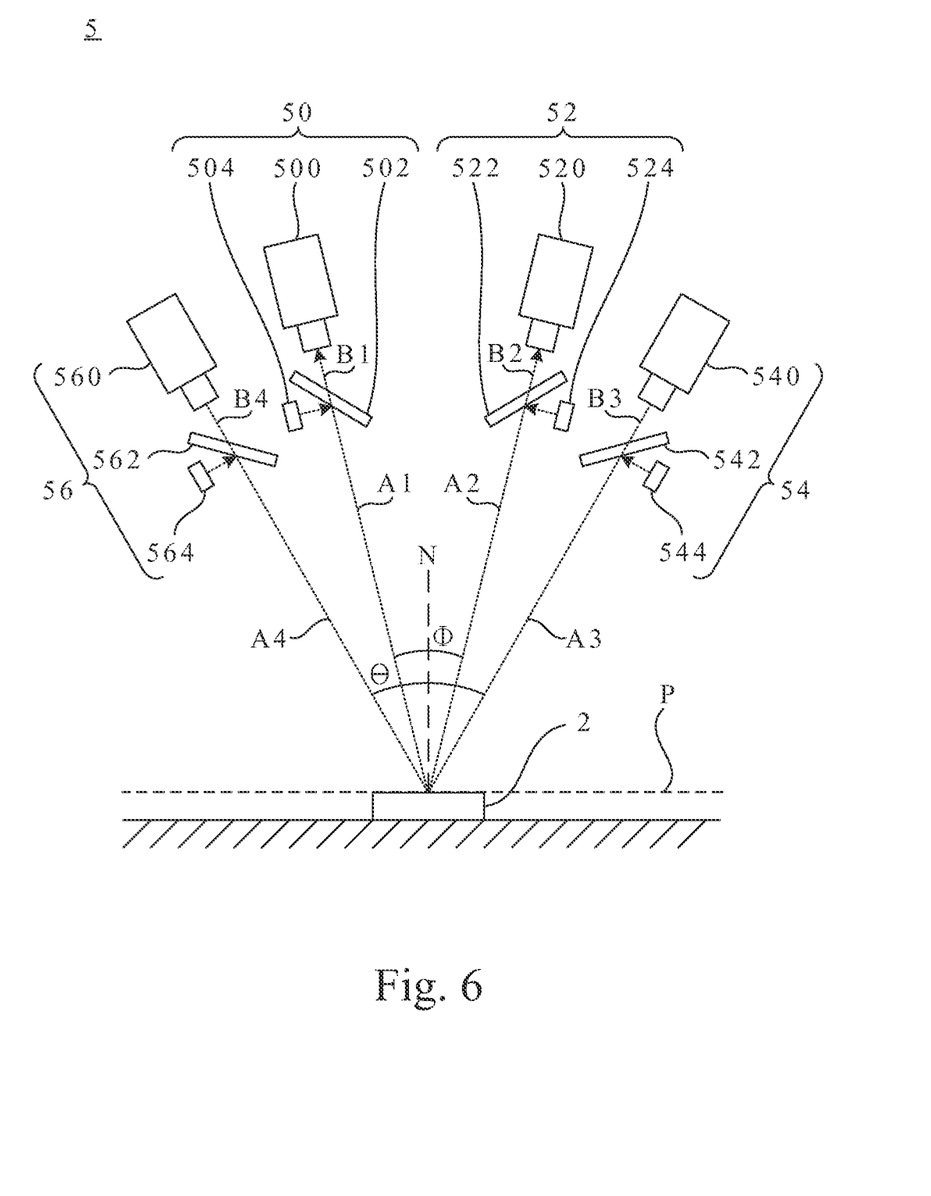
FIG. 6 is a schematic diagram illustrating an optical inspection system according to another embodiment of the disclosure.

FIG. 6 is a schematic diagram illustrating an optical inspection system 5 according to another embodiment of the disclosure. As shown in FIG. 6, the optical inspection system 5 is also used to inspect a DUT 2. The optical inspection system 5 includes a first optical module 50 and a second optical module 52. The first optical module 50 includes a first image capturing unit 500, a first filter 502, and a first light source 504. The first image capturing unit 500 has a first image capturing axis B1 aligned with the DUT 2. The first filter 502 is located on the first image capturing axis B1 and has a first transmission spectrum. The first light source 504 is used to emit light toward the first filter 502. The first filter 502 is configured to reflect most of the light emitted by the first light source 504. The reflected light of the first light source 504 has a first optical axis A1 substantially coinciding with the first image capturing axis B1.

The second optical module 52 includes a second image capturing unit 520, a second filter 522, and a second light source 524. The second image capturing unit 520 has a second image capturing axis B2 aligned with the DUT 2. The second image capturing axis B2 and the first image capturing axis B1 are symmetric relative to a normal line N of an inspection plane P on the DUT 2. The second filter 522 is located on the second image capturing axis B2 and has a second transmission spectrum shifted away from the first transmission spectrum. The second light source 524 is used to emit light toward the second filter 522. The second filter 522 is configured to reflect most of the light emitted by the second light source 524. The reflected light of the second light source 524 has a second optical axis A2 substantially coinciding with the second image capturing axis B2.

The first filter 502 is further configured to transmit most of the light emitted by the second light source 524, and the second filter 522 is further configured to transmit most of the light emitted by the first light source 504. In other words, the transmittance of the light emitted by the first light source 504 through the second filter 522 is much greater than the transmittance of the light emitted by the second light source 524 through the second filter 522, and the transmittance of the light emitted by the first light source 504 through the first filter 502 is much smaller than the transmittance of the light emitted by the second light source 524 through the first filter 502.

As shown in FIG. 4A and FIG. 4B, it is clear that the second transmission spectrum is shifted away from the first transmission spectrum. As shown in FIG. 5A and FIG. 5B, the light emitted by the first light source 504 has the first triplet R1, G1, B1 substantially matching the second transmission spectrum, and the light emitted by the second light source 524 has the second triplet R2, G2, B2 substantially matching the first transmission spectrum. Accordingly, the purpose of configuring the first and second filters 502, 522 such that the first filter 502 transmits most of the light emitted by the second light source 524 and reflects most of the light emitted by the first light source 504, and the second filter 522 reflects most of the light emitted by the second light source 524 and transmits most of the light emitted by the first light source 504 can be achieved.

With the foregoing configuration, the first light source 504 and the second light source 524 can emit light toward the DUT 2 at the same time, and the first image capturing unit 500 and the second image capturing unit 520 can capture images of the DUT 2 at the same time, so as to improve the inspection efficiency of the optical inspection system 5.

In the embodiment of the disclosure, even if the DUT 2 has a mirror surface on the inspection plane P, a large amount of the emitted light of the first light source 504 can be reflected to the second image capturing unit 520 because the arrangement of the first optical axis A1 and the second image capturing axis B2 is in accordance with the law of reflection, and similarly, a large amount of the emitted light of the second light source 524 can be reflected to the first image capturing unit 500 because the arrangement of the second optical axis A2 and the first image capturing axis B1 is also in accordance with the law of reflection.

In an embodiment of the disclosure, the first optical module 50 is located at a side of the normal line N (i.e., the left side of the normal line N), and the second optical module 52 is located at another side of the normal line N (i.e., the right side of the normal line N). That is, the first light source 504 and the second light source 524 are respectively located at two opposite sides of the DUT 2 relative to the normal line N. As mentioned above, the first image capturing unit 500 and the second image capturing unit 520 can capture images at the same time. Through such a configuration, even if the left part of the image captured by the first image capturing unit 500 and the right part of the image captured by the second image capturing unit 520 have shadows (because the first filter 502 and the second filter 522 only allow for transmitting of the light emitted by the second light source 524 and the first light source 504 respectively), the captured images can be analyzed and synthesized to obtain a synthetic image without shadows. The three-dimensional shape of the DUT 2 can then be calculated from the synthetic image by using an algorithm. Accordingly, the problem of shadows can also be solved by the optical inspection system 5 of this embodiment.

In an embodiment of the disclosure, each of the first and second light sources 504, 524 emits unpolarized light. Although the first light source 504 and the second light source 524 emit the unpolarized light toward the DUT 2 with different incident angles, a better uniformity can be obtained.

In an embodiment of the disclosure, each of the first and second light sources 504, 524 emits polarized light. In order to obtain better image contrast when analyzing certain defects or sloped surfaces, polarized light can be used.

As shown in FIG. 6, the optical inspection system 5 further includes a third optical module 54 and a fourth optical module 56. The third optical module 54 includes a third image capturing unit 540, a third filter 542, and a third light source 544. The third image capturing unit 540 has a third image capturing axis B3 aligned with the DUT 2. The third filter 542 is located on the third image capturing axis B3 and has the first transmission spectrum. The third light source 544 is used to emit light toward third filter 542. The third filter 542 is configured to reflect most of the light emitted by the third light source 544. The reflected light of the third light source 544 has a third optical axis A3 substantially coinciding with the third image capturing axis B3. The fourth optical module 56 includes a fourth image capturing unit 560, a fourth filter 562, and a fourth light source 564. The fourth image capturing unit 560 has a fourth image capturing axis B4 aligned with the DUT 2. The fourth image capturing axis B4 and the third image capturing axis B3 are symmetric relative to the normal line N. The fourth filter 562 is located on the fourth image capturing axis B4 and has the second transmission spectrum. The fourth light source 564 is used to emit light toward the fourth filter 562. The fourth filter 562 is configured to reflect most of the light emitted by the fourth light source 564. The reflected light of the fourth light source 564 has a fourth optical axis A4 substantially coinciding with the fourth image capturing axis B4.

It is noted that the third filter 542 is further configured to transmit most of the light emitted by the fourth light source 564, and the fourth filter 562 is further configured to transmit most of the light emitted by the third light source 544. In other words, the transmittance of the light emitted by the third light source 544 through the fourth filter 562 is much greater than the transmittance of the light emitted by the fourth light source 564 through the fourth filter 562, and the transmittance of the light emitted by the third light source 544 through the third filter 542 is much smaller than the transmittance of the light emitted by the fourth light source 564 through the third filter 542.

As shown in FIG. 4A and FIG. 4B, it is clear that the second transmission spectrum is shifted away from the first transmission spectrum. With reference to FIG. 5A and FIG. 5B, the light emitted by the third light source 544 has the first triplet R1, G1, B1 substantially matching the second transmission spectrum, and the light emitted by the fourth light source 564 has the second triplet R2, G2, B2 substantially matching the first transmission spectrum. Accordingly, the purpose of configuring the third filter 542 such that the third filter 542 transmits most of the light emitted by the fourth light source 564 and reflects most of the light emitted by the third light source 544, and configuring the fourth filter 562 such that the fourth filter 562 reflects most of the light emitted by the fourth light source 564 and transmits most of the light emitted by the third light source 544 can be achieved.

With the foregoing configuration, the third light source 544 and the fourth light source 564 can emit light toward the DUT 2 at the same time, and the third image capturing unit 540 and the fourth image capturing unit 560 can capture images of the DUT 2 at the same time, so as to improve the inspection efficiency of the optical inspection system 5.

In the embodiment of the disclosure, even if the DUT 2 has a mirror surface on the inspection plane P, a large amount of the emitted light of the third light source 544 can be reflected to the fourth image capturing unit 560 because the arrangement of the third optical axis A3 and the fourth image capturing axis B4 is in accordance with the law of reflection, and similarly, a large amount of the emitted light of the fourth light source 564 can be reflected to the third image capturing unit 540 because the arrangement of the fourth optical axis A4 and the third image capturing axis B3 is also in accordance with the law of reflection.

In an embodiment of the disclosure, the third optical module 54 is located at a side of the normal line N (i.e., the right side of the normal line N), and the fourth optical module 56 is located at another side of the normal line N (i.e., the left side of the normal line N). That is, the third light source 544 and the fourth light source 564 are respectively located at two opposite sides of the DUT 2 relative to the normal line N. As mentioned above, the third image capturing unit 540 and the fourth image capturing unit 560 can capture images at the same time. Through such a configuration, even if the right part of the image captured by the third image capturing unit 540 and the left part of the image captured by the fourth image capturing unit 560 have shadows (because the third filter 542 and the fourth filter 562 only allow for transmitting of the light emitted by the fourth light source 564 and the third light source 544 respectively), the captured images can be analyzed and synthesized to obtain a synthetic image without shadows. The three-dimensional shape of the DUT 2 can then be calculated from the synthetic image by using an algorithm. Accordingly, the problem of shadows can also be solved by the optical inspection system 5 of this embodiment.

In an embodiment of the disclosure, a first angle $\varphi$ is formed between the first image capturing axis B1 and the second image capturing axis B2. A second angle $\theta$ is formed between the third image capturing axis B3 and the fourth image capturing axis B4, and the second angle $\theta$ is different from the first angle $\varphi$. The optical inspection system 5 of this embodiment is configured such that the first angle $\varphi$ between the first image capturing axis B1 of the first optical module 50 and the second image capturing axis B2 of the second optical module 52 is different from the second angle $\theta$ between the third image capturing axis B3 of the third optical module 54 and the fourth image capturing axis B4 of the fourth optical module 56, so as to improve the inspecting capability of particles and short circuit problems on the DUT 2.

In an embodiment of the disclosure, the first and second angles $\varphi$, $\theta$ are ranged from 55 to 65 degrees, but the disclosure is not limited in this regard.

In an embodiment of the disclosure, each of the third and fourth light sources 544, 564 emits unpolarized light. Although the third light source 544 and the fourth light source 564 emit unpolarized light toward the DUT 2 with different incident angles, a better uniformity can be obtained.

In an embodiment of the disclosure, each of the third and fourth light sources 544, 564 emits polarized light. In order to obtain better image contrast when analyzing certain defects or sloped surfaces, polarized light can be used.

It is noted that the optical inspection system 5 of this embodiment utilizes four sets of optical modules, so that this embodiment can obtain more information than the embodiment of FIG. 3.

According to the foregoing recitations of the embodiments of the disclosure, it can be seen that the optical inspection system of the disclosure arranges the optical axis of each of the light sources and the image capturing axis of the corresponding image capturing unit to be symmetric relative to the normal line of the inspection plane, so that even if the DUT has a mirror surface at the inspection plane, a large amount of the emitted light of each light source can be reflected to the corresponding image capturing unit. The optical inspection system of the disclosure further locates the light sources at two opposite sides of the DUT relative to the normal line respectively, so that even if the images captured by the image capturing units have shadows at different locations, the images can be further analyzed and synthesized to obtain a synthetic image without shadows, and thus the problem of shadows can be solved. Furthermore, the optical inspection system of the disclosure is configured such that the angle between the optical axis and the corresponding image capturing unit in an optical module be different from that in another optical module, so as to improve the inspecting capability of particles and short circuit problems. Moreover, by adjusting the above-mentioned angles, the measurement range of the optical inspection system can be enlarged. In addition, by using filters that each only allows for transmitting of most of the light emitted by the corresponding light source, all of the image capturing units can capture images at the same time, so as to improve the inspection efficiency of the optical inspection system.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure covers modifications and variations of this disclosure provided they fall within the scope of the following claims.

What is claimed is:

1. An optical inspection system for inspecting a device under test, the optical inspection system comprising:
    a first optical module, comprising:
      a first light source having a first optical axis; and
      a first image capturing unit having a first light receiving surface and a first image capturing axis perpendicular to the first light receiving surface, wherein the first optical axis and the first image capturing axis are symmetric relative a normal line of an inspection plane on the device under test, and a first angle is formed between the first optical axis and the first image capturing axis; and
    a second optical module, comprising:
      a second light source having a second optical axis; and
      a second image capturing unit having a second light receiving surface and a second image capturing axis perpendicular to the second light receiving surface, wherein the second optical axis and the second image capturing axis are symmetric relative to the normal line, a second angle is formed between the second optical axis and the second image capturing axis, and the second angle is different from the first angle.

2. The optical inspection system of claim 1, wherein the first light source and the second image capturing unit are located at a side of the normal line, and the second light source and the first image capturing unit are located at another side of the normal line.

3. The optical inspection system of claim 1, wherein the first and second angles are ranged from 55 to 65 degrees.

4. The optical inspection system of claim 1, wherein the first and second light sources emit unpolarized light or polarized light.

5. The optical inspection system of claim 1, wherein light emitted by the first light source generates a first fringe pattern on the device under test, the first fringe pattern has a first stripe pitch, light emitted by the second light source generates a second fringe pattern on the device under test, and the second fringe pattern has a second stripe pitch equal to the first stripe pitch.

6. The optical inspection system of claim 1, wherein light emitted by the first light source generates a first fringe pattern on the device under test, the first fringe pattern has a first stripe pitch, light emitted by the second light source generates a second fringe pattern on the device under test, and the second fringe pattern has a second stripe pitch different from the first stripe pitch.

7. An optical inspection system for inspecting a device under test, the optical inspection system comprising:
    a first optical module, comprising:
      a first light source having a first optical axis;
      a first image capturing unit having a first light receiving surface and a first image capturing axis perpendicular to the first light receiving surface, wherein the first optical axis and the first image capturing axis are symmetric relative a normal line of an inspection plane on the device under test, and a first angle is formed between the first optical axis and the first image capturing axis; and
      a first filter located on the first image capturing axis and having a first transmission spectrum; and
    a second optical module, comprising:
      a second light source having a second optical axis;
      a second image capturing unit having a second light receiving surface and a second image capturing axis perpendicular to the second light receiving surface, wherein the second optical axis and the second image capturing axis are symmetric relative to the normal line, a second angle is formed between the second optical axis and the second image capturing axis, and the second angle is different from the first angle; and
      a second filter located on the second image capturing axis and having a second transmission spectrum shifted away from the first transmission spectrum,
    wherein the first filter is configured to transmit light emitted by the first light source and to reflect light emitted by the second light source, and the second filter is configured to reflect the light emitted by the first light source and to transmit light emitted by the second light source.

8. The optical inspection system of claim 7, wherein the light emitted by the first light source has a first triplet substantially matching the first transmission spectrum, and the light emitted by the second light source has a second triplet substantially matching the second transmission spectrum.

9. The optical inspection system of claim 7, wherein the first light source, the second filter, and the second image capturing unit are located at a side of the normal line, and the second light source, the first filter, and the first image capturing unit are located at another side of the normal line.

10. The optical inspection system of claim 7, wherein the first and second angles are ranged from 55 to 65 degrees.

11. The optical inspection system of claim 7, wherein the first and second light sources emit unpolarized light or polarized light.

12. An optical inspection system for inspecting a device under test, the optical inspection system comprising:
    a first optical module, comprising:
      a first image capturing unit having a first light receiving surface and a first image capturing axis perpendicular to the first light receiving surface;
      a first filter located on the first image capturing axis and having a first transmission spectrum; and
      a first light source for emitting light toward the first filter, wherein the first filter is configured to reflect light emitted by the first light source, and the reflected light of the first light source has a first optical axis substantially coinciding with the first image capturing axis;

a second optical module, comprising:
a second image capturing unit having a second light receiving surface and a second image capturing axis perpendicular to the second light receiving surface, wherein the second image capturing axis and the first image capturing axis are symmetric relative to a normal line of an inspection plane on the device under test;
a second filter located on the second image capturing axis and having a second transmission spectrum shifted away from the first transmission spectrum; and
a second light source for emitting light toward the second filter, wherein the second filter is configured to reflect light emitted by the second light source, and the reflected light of the second light source has a second optical axis substantially coinciding with the second image capturing axis;
wherein the first filter is further configured to transmit the light emitted by the second light source, and the second filter is further configured to transmit the light emitted by the first light source.

13. The optical inspection system of claim 12, wherein the light emitted by the first light source has a first triplet substantially matching the second transmission spectrum, and the light emitted by the second light source has a second triplet substantially matching the first transmission spectrum.

14. The optical inspection system of claim 12, wherein the first optical module is located at a side of the normal line, and the second optical module is located at another side of the normal line.

15. The optical inspection system of claim 12, wherein the first and second light sources emit unpolarized light or polarized light.

16. The optical inspection system of claim 12, wherein a first angle is formed between the first image capturing axis and the second image capturing axis, and the optical inspection system further comprises:
a third optical module, comprising:
a third image capturing unit having a third image capturing axis;
a third filter located on the third image capturing axis and having the first transmission spectrum; and
a third light source for emitting light toward third filter, wherein the third filter is configured to reflect light emitted by the third light source, and the reflected light of the third light source has a third optical axis substantially coinciding with the third image capturing axis;
a fourth optical module, comprising:
a fourth image capturing unit having a fourth image capturing axis, wherein the fourth image capturing axis and the third image capturing axis are symmetric relative to the normal line, a second angle is formed between the third image capturing axis and the fourth image capturing axis, and the second angle is different from the first angle;
a fourth filter located on the fourth image capturing axis and having the second transmission spectrum; and
a fourth light source for emitting light toward the fourth filter, wherein the fourth filter is configured to reflect light emitted by the fourth light source, and the reflected light of the fourth light source has a fourth optical axis substantially coinciding with the fourth image capturing axis;
wherein the third filter is further configured to transmit the light emitted by the fourth light source, and the fourth filter is further configured to transmit the light emitted by the third light source.

17. The optical inspection system of claim 16, wherein the light emitted by the third light source has a first triplet substantially matching the second transmission spectrum, and the light emitted by the fourth light source has a second triplet substantially matching the first transmission spectrum.

18. The optical inspection system of claim 16, wherein the third optical module is located at a side of the normal line, and the fourth optical module is located at another side of the normal line.

19. The optical inspection system of claim 16, wherein the first and second angles are ranged from 55 to 65 degrees.

20. The optical inspection system of claim 16, wherein the third and fourth light sources emit unpolarized light or polarized light.

* * * * *